United States Patent [19]

Welter et al.

[11] 4,370,345
[45] Jan. 25, 1983

[54] PHENOXYPHENYLPROPENYLOXYCARBONYL COMPOUNDS AND THEIR USE AS INSECTICIDES AND ACARICIDES

[75] Inventors: Wolfgang Welter; Hilmar Mildenberger, both of Kelkheim; Werner Knauf; Anna Waltersdorfer, both of Frankfurt am Main; Werner Bonin, Kelkheim, all of Fed. Rep. of Germany

[73] Assignee: Hoechst Aktiengesellschaft, Frankfurt am Main, Fed. Rep. of Germany

[21] Appl. No.: 315,150

[22] Filed: Oct. 26, 1981

[30] Foreign Application Priority Data

Oct. 28, 1980 [DE] Fed. Rep. of Germany ....... 3040488

[51] Int. Cl.³ .................... A01N 43/30; A01N 53/00; C07C 69/743; C07C 121/75
[52] U.S. Cl. ................... 424/282; 260/465 D; 424/304; 424/305; 424/308; 549/442; 549/447; 560/8; 560/9; 560/18; 560/55; 560/73; 560/102; 560/105; 560/124
[58] Field of Search ................. 260/465 D; 560/124, 560/8, 9, 18, 55, 73, 102, 105; 424/304, 305, 282, 308; 549/442, 447

[56] References Cited

U.S. PATENT DOCUMENTS 3,981,903 9/1976 Hirano et al. .................. 560/124 X
4,118,505 10/1978 Kitamura et al. ............... 560/124 X Primary Examiner—Dolph H. Torrence
Attorney, Agent, or Firm—Curtis, Morris & Safford

[57] ABSTRACT

Compounds of the formula

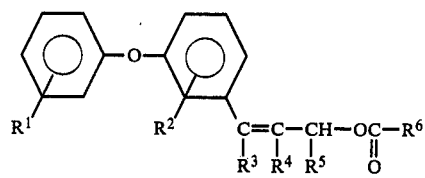

wherein $R^1$ denotes H, halogen, alkyl or $CF_3$, $R^2$ denotes H, halogen, alkyl or $CF_3$, $R^3$ denotes H, halogen, CN or alkyl, $R^4$ denotes H, halogen, alkyl, phenyl or halogenophenyl, $R^5$ denotes H, alkyl, alkynyl or CN and $R^6$ denotes substituted dimethylcyclopropyl or 2-phenylisobutyl radicals, are effective insecticides and acaricides of the pyrethroid type.

14 Claims, No Drawings

PHENOXYPHENYLPROPENYLOXYCARBONYL COMPOUNDS AND THEIR USE AS INSECTICIDES AND ACARICIDES

It is already known that phenylpropenyloxy compounds of halogen-substituted vinylcyclopropanecarboxylic acids possess insecticidal properties (compare German Offenlegungsschriften Nos. 2,647,366 and 2,925,315).

The present invention relates to new substituted phenoxyphenylpropenyloxycarbonyl compounds of the formula

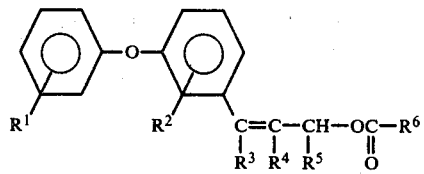
(I)

in which $R^1$ denotes hydrogen, halogen, $C_1$-$C_4$ alkyl or $C_1$-$C_4$ alkoxy, $R^2$ denotes hydrogen, halogen, $C_1$-$C_4$ alkyl or trifluoromethyl, $R^3$ denotes hydrogen, halogen, cyano or $C_1$-$C_4$ alkyl, $R^4$ denotes hydrogen, halogen, $C_1$-$C_4$ alkyl, phenyl or halogenophenyl, $R^5$ denotes hydrogen, $C_1$-$C_4$ alkyl, $C_2$-$C_3$ alkynyl or cyano, $R^6$ denotes a radical of the formula

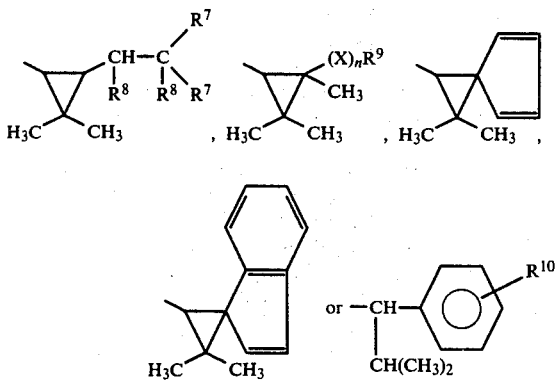

$R^7$ denotes halogen, $C_1$-$C_4$ alkyl, phenyl or halogenophenyl, $R^8$ denotes halogen or the two $R^8$s together denote a further chemical bond, $R^9$ denotes $C_1$-$C_4$ alkyl, phenyl or halogenophenyl, $R^{10}$ denotes hydrogen, halogen, $C_1$-$C_4$ alkyl, $C_1$-$C_4$ alkoxy, $C_1$-$C_4$ alkylthio, halogeno-($C_1$-$C_4$) alkoxy, halogeno-($C_1$-$C_4$) alkylthio or methylenedioxy, X denotes oxygen or sulfur and n denotes 0 or 1.

In this connection, the general formula (I) includes the various optical and geometrical isomers of the compounds and mixtures thereof.

In the above definitions, "halogen" preferably denotes Br and Cl and, in the case of the radicals $R^1$, $R^2$ and $R^{10}$, also F.

The new compounds of the formula (I) are distinguished by a strong insecticidal and acaricidal activity.

The compounds of the formula (I) are obtained (a) by reacting carboxylic acids of the formula $R^6$-COOH (II) or reactive functional derivatives thereof with alcohols of the formula

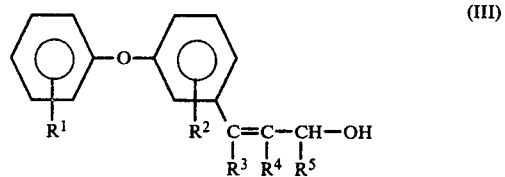
(III)

or (b) by reacting carboxylic acid halides of the formula $R^6$-CO-Hal (IV) with aldehydes of the formula

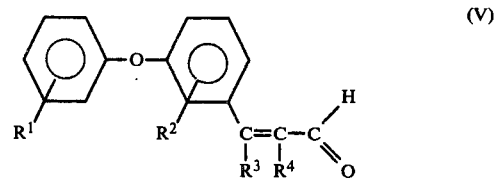
(V)

in the presence of at least an equimolar quantity of alkali metal cyanide and, if appropriate, in the presence of a catalyst.

In regard to (a), examples of suitable functional derivatives of carboxylic acids of the formula (II) are acid halides, acid anhydrides or esters. The reaction is generally carried out using diluents. Suitable diluents are virtually any inert organic solvents.

The following may be mentioned as examples: aliphatic and aromatic hydrocarbons, which may be chlorinated, for example pentane, hexane, heptane, benzene, toluene, xylene, methylene chloride, chloroform, carbon tetrachloride, chlorobenzene and dichlorobenzene; ethers, such as, for example, diethyl ether, tetrahydrofuran and dioxane, and also nitriles, such as, for example, acetonitrile and propionitrile.

If the acid halides (preferably the acid chlorides) of the formula (IV) are used as the starting materials, it is appropriate to add an acid acceptor. The customary acid binding agents can be used for this purpose, for example alkali metal carbonates, such as sodium carbonate and potassium carbonate; alkali metal alcoholates, such as sodium methylate or ethylate and potassium methylate or ethylate, and also aliphatic, aromatic or heterocyclic amines, such as trimethylamine, triethylamine, dimethylaniline, dimethylbenzylamine and pyridine.

In regard to (b), catalysts which are used for variant (b) of the process according to the invention are, in general, compounds which are usually employed as auxiliaries for the phase transfer of reactants in reactions in a multi-phase medium. Tetraalkylammonium and trialkylarylammonium salts should be mentioned in particular, such as, for example, tetrabenzylammonium chloride, bromide or iodide and triethylbenzylammonium chloride. Examples of alkali metal cyanides which can be used are sodium cyanide and potassium cyanide. The solvents are the same as those in (a); if the reaction is carried out in a two-phase system, water can also be added as a solvent component. In all cases the reaction temperature can be varied within a fairly wide range. In general, the reaction is carried out between 0° and 100° C., preferably between 10° and 50° C. In general, the reactions are carried out under normal pressure.

The starting components are generally employed in equimolar quantities. An excess of one or other of the components yields no appreciable advantages. The components are generally added in one or more of the diluents indicated and are stirred for several hours in order to complete the reaction. The mixture is then shaken with toluene/water and the organic phase is separated off, washed with water and dried. After removing the solvent by distillation in vacuo, the new compounds are generally obtained in the form of oils which cannot be distilled without decomposition. They can, however, be freed from the last volatile constituents, and purified in this manner, by so-called "incipient distillation", that is to say by prolonged heating at moderately elevated temperatures under reduced pressure. They are characterized by means of the refractive index.

The carboxylic acids of the formula (II) or reactive derivatives thereof, such as acid chlorides or esters, which are to be used as starting compounds are known (compare German Offenlegungsschriften Nos. 1,926,433, 2,231,312, 2,365,555, 2,605,828, 2,738,150, 2,544,150 and 2,742,546).

In addition to those used in the examples, the following may be mentioned as examples of acid chlorides:

2,2-dimethyl-3-(2-phenylvinyl)-cyclopropane-1-carboxylic acid chloride, 2,2-dimethyl-3-(2-(4-chlorophenyl)-vinyl)-cyclopropane-1-carboxylic acid chloride, 2,2,3,3-tetramethylcyclopropane-1-carboxylic acid chloride, 2,2-dimethylspiro(2,4)hepta-4,6-diene-1-carboxylic acid chloride, 3,3-dimethylspirocyclopropane-1,1'-indene-2-carboxylic acid chloride, α-isopropyl-4-trifluoromethylphenylacetic acid chloride, α-isopropyl-4-methoxyphenylacetic acid chloride, α-isopropyl-4-trifluoromethoxyphenylacetic acid chloride, α-isopropyl-4-methylthiophenylacetic acid chloride, α-isopropyl-4-trifluoromethylthiophenylacetic acid chloride and α-isopropyl-3,4-methylene-dioxyphenylacetic acid chloride.

The compounds according to the invention have an excellent action against sucking and biting insects and also against species belonging to the order Acarina When used against insects and mites which damage plants, they are distinguished, not only by contact action and ingested poison action, but also by being well tolerated by plants. In addition, they are also effective against pests of stored products and also against species belonging to the group of hygiene pests.

Thus it is possible to combat effectively various species of spider mites, such as the fruit tree red spider mite (*Panonychus ulmi*), the citrus spider mite (*Panonychus citri*) and the red spider mite (*Tetranychus urticae*).

Many harmful insects having sucking and biting mouth-parts can also be destroyed by means of the compounds according to the invention.

Mention may be made of beetles, such as the Mexican bean beetle (*Epilachna varivestis*) the Colorado beetle (*Leptinotarsa decemlineata*), the turnip flea beetle (Phyllotreta spp.), strawberry rhynchites (*Caenorrhinus germanicus*), the strawberry blossom weevil (*Anthonomus rubi*), the boll-weevil (*Anthonomus grandis*), wire worms (Agriotes spec.), butterflies and their larvae, such as the osier green moth and the bollworm (*Earias insulana* and *Heliothis armigera*, respectively) and the tobacco budworm (*Heliothis virescens*); tortrix moths, in particular codling moths (*Carpocapsa pomonella*), green oak ortrix moths (*Tortrix viridana*), summer fruit tortrix moths (*Adoxophyes reticulana*), fruit tree tortrix moths (*Hedya nubifernana*), vine moths (*Eupoecilia ambiguella*), European corn borers (*Ostrinia nubilalis*), cutworms (Agrotis spec.), winter moths (*Operophthera brumata*) and nun moths (*Lymantria monacha*), and also flies, such as beet flies (*Pegomya betae*) and Mediterranean fruitfly (*Ceratitis capitata*), and blackbeetles, such as the cockroach (*Blatta germanica*) and the oriental cockroach (*Blatta orientalis*) and aphids, such as the bean aphid (*Doralis fabae*), the green peach aphid (*Myzus persicae*) and the cotton aphid (*Aphis gossypii*), and bugs, for example cotton bugs (*Oncopeltus fasciatus* and Dysdercus spp.). The activity of the compounds according to the invention extends to all the development stages or individual development stages of normally sensitive and resistant species.

The compounds of the formula (I) also have an excellent activity against ectoparasites in animals. The have a good action both against permanently and temporarily parasitic insects and against mites and, in particular, against ticks.

The animal ectoparasites belonging to the class of insects, against which the compounds of the formula (I) are active, include sucking lice (Anoplura), fleas (Ceratophyllidae) and biting lice and bird lice (Mallophage) and also flies, such as stable flies (Stomoxydidae) and gadflies (Tabanidae), as well as flies in which the development forms (larvae) are parasitic as pests in the body of an animal (Calliphoridae, Sarcophagidae, Gastrophilidae and Oestridae) and, finally, louse flies (Hippoboscidae). Ectoparasites belonging to the order of mites (Acaridae) are mange mites (Sarcoptidae), poultry mites (Dermanyssidae), leathery ticks (Argasidae) and finally hard ticks (Ixodidae), including particularly the monoxenous cattle ticks Boophilus microplus and Boophilus decoloratus as well as the heteroxenous species of the genera Rhipicephalus, Amblyomma and Hyalomma.

In general, the agents according to the invention contain the active compounds of the formula (I) to the extent of 2-95% by weight, preferably 5-90% by weight. They can be applied in the customary formulations, in the form of wettable powders, emulsifiable concentrates, sprayable solutions, dusting agents, dressing agents, dispersions, granules or microgranules.

Wettable powders are preparations which can be dispersed homogeneously in water and which, besides the active compound and apart from a diluent or inert substance, if appropriate, also contain wetting agents, for example polyoxyethylated alkylphenols, polyoxyethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltauride. They are prepared in a customary manner, for example by grinding and mixing the components.

Emulsifiable concentrates can be prepared, for example, by dissolving the active compound in an inert organic solvent, for example butanol, cyclohexanone, dimethylformamide, xylene or fairly high-boiling aromatic solvents or hydrocarbons, with the addition of one or more emulsifiers. In the case of liquid active compounds, the solvent component can also be omitted partially or entirely. The following are examples of emulsifiers which can be used:

Calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylenesorbitan fatty acid esters or polyoxethylenesorbitol esters.

Dusting agents can be obtained by grinding the active compound with finely divided solids, for example talc, natural clays, such as kaolin, bentonite or pyrophillite, or diactomaceous earth.

Granules can be prepared either by atomizing the active compound onto an adsorbent granulated inert material, or by applying active compound concentrates by means of binders, for example polyvinyl alcohol, sodium polyacrylate or mineral oils, to the surface of carriers, such as sand, kaolinite or granulated inert material. Suitable active compounds can also be granulated in the manner customary for the production of fertilizer granules-if desired as a mixture with fertilizers.

The concentration of active compound in wettable powders is, for example, about 10 to 90% by weight; the remainder up to 100% by weight consists of customary formulation ingredients. In the case of emulsifiable concentrates, the concentration of active compound can be about 10 to 80% by weight. Formulations in dust form in most cases contain 5 to 20% by weight of active compound. In the case of granules, the content of active compound depends in part on whether the active compound is present in a liquid or solid state and on which granulating auxiliaries, fillers and the like are used.

In addition, the said formulations of active compounds contain, if appropriate, the adhesives, wetting agents, dispersing agents, emulsifiers, penetration agents, solvents, fillers or carriers which are customary in each particular case.

For application, the concentrates present in a commercial form are, if appropriate, diluted in a customary manner, for example with water in the case of wettable powders, emulsifiable concentrates and dispersions and, in some cases, also in the case of microgranules. Formulations in the form of dust and granules and sprayable solutions are usually not diluted further with other inert substances before use. The acaricidal and/or insecticidal action can be broadened and adapted to given circumstances by adding other insecticides and/or acaricides. Examples of suitable additives are organic phosphorus compounds; nitrophenols and derivatives thereof; formamidines; ureas; other pyrethrin-like compounds and also carbamates and chlorinated hydrocarbons.

The application of the active compounds to be used in accordance with the invention in the veterinary field is usually effected by the spraying, atomizing, dusting or bath process, and, in the special case of tick agents, in so-called dip or spray installations.

It is particularly advantageous to combine compounds of the formula (I) with substances which exert a synergistic or potentiating effect on pyrethroids. Examples of such compounds are, inter alia, piperonyl butoxide, propynyl ethers, propynyl oximes, propynyl carbamates and propynyl phosphonates, 2-(3,4-methylenedioxyphenoxy)-3,6,9-trioxaundecane, S,S,S,-tributyl phosphorotrithioates and 1,2-methylenedioxy-4-[2-(octylsulfinyl)-propyl]-benzene.

The invention is illustrated in greater detail by means of the following examples:

Preparation Examples

Example 1

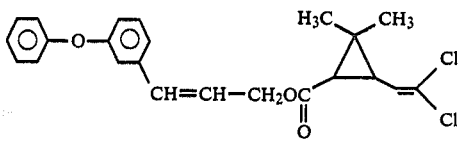

A solution of 9.04 g (0.04 mole) of 3-phenoxycinnamyl alcohol and 3.3 g of pyridine in 30 ml of toluene is added dropwise, at 25° C., to a solution of 9.1 g (0.04 mole) of 3-(2,2-dichlorovinyl)-2,2-dimethylcyclopropane-1-carboxylic acid chloride (cis/trans ratio 50:50) in 40 ml of toluene, and the mixture is stirred for a further four hours at 25° C. The mixture is poured into 100 ml of water and the organic phase is separated off and washed with dilute hydrochloric acid and with water. The toluene phase is then dried over sodium sulfate. After removing the solvent in vacuo and a brief incipient distillation at 50° C./0.5 mm Hg, in order to remove the last residues of solvent, 16.18 g (97% of theory) of 3-(3-phenoxyphenyl)-2-propen-1-yl 3-(2,2-dichlorovinyl)-2,2-dimethylcyclopropane-1-carboxylate are obtained in the form of a pale yellow oil having a refractive index $n_D^{20}$ of 1.5850.

EXAMPLE 2

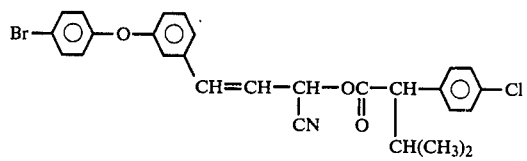

A solution of 5.78 g (0.025 mole) of α-isopropyl-4-chlorophenylacetyl chloride and 7.55 g (0.025 mole) of 3-(4-bromophenoxy)-cinnamaldehyde is added dropwise, at 25° C., to a mixture of 2.5 g of sodium cyanide, 2.5 ml of water, 50 ml of n-hexane and 0.2 g of tetrabutylammonium iodide, and the mixture is stirred for 5 hours at 25° C. 300 ml of toluene and 200 ml of water are then added to the reaction mixture and the mixture is stirred for 30 minutes and the organic phase is separated off. The toluene phase is shaken with saturated sodium chloride solution and dried over sodium sulfate. After removing the solvent in vacuo and a brief incipient distillation at 50° C./0.5 mm Hg, 9.62 g (73% of theory) of 3-[3-(4-bromophenoxy)-phenyl]-2-propen-1-yl 2-(4-chlorophenyl)-isovalerate are obtained. Refractive index $n_D^{21} = 1.5968$.

The compounds of the formula (I) can be prepared analogously to Example 1 or 2

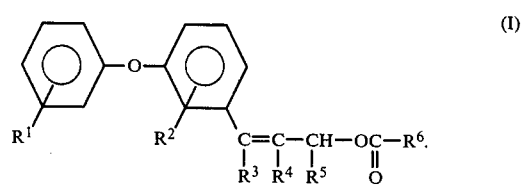

(I)

| Example | $R^1$ | $R^2$ | $R^3$ | $R^4$ | $R^5$ | $R^6$ | $n_D$ |
|---|---|---|---|---|---|---|---|
| 3 | H | H | H | H | CN | 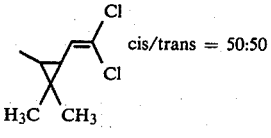 cis/trans = 50:50 | $n_D^{20}$ = 1.5839 |
| 4 | H | H | H | H | C≡CH | " | $n_D^{24}$ = 1.5748 |
| 5 | H | H | H | H | $CH_3$ | " | $n_D^{21}$ = 1.5708 |
| 6 | 4-Br | H | H | H | H | " | $n_D^{22}$ = 1.5942 |
| 7 | 4-Br | H | H | H | CN | " | $n_D^{21}$ = 1.6039 |
| 8 | 4-Br | H | H | H | C≡CH | " | |
| 9 | 4-Br | H | H | H | $CH_3$ | " | $n_D^{23}$ = 1.5878 |
| 10 | 4-Cl | H | H | H | H | " | $n_D^{21}$ = 1.5890 |
| 11 | 4-Cl | H | H | H | CN | " | |
| 12 | 4-Cl | H | H | H | C≡CH | " | |
| 13 | 4-$CH_3$ | H | H | H | H | " | $n_D^{25}$ = 1.5768 |
| 14 | 4-$CH_3$ | H | H | H | CN | " | $n_D^{20}$ = 1.5837 |
| 15 | 4-$CH_3$ | H | H | H | C≡CH | (as Example 3) | |
| 16 | 4-F | H | H | H | H | " | $n_D^{26}$ = 1.5749 |
| 17 | 4-F | H | H | H | CN | " | |
| 18 | 4-F | H | H | H | C≡CH | " | |
| 19 | 4-$OCH_3$ | H | H | H | H | " | $n_D^{19}$ = 1.5818 |
| 20 | 4-$OCH_3$ | H | H | H | CN | " | |
| 21 | 3-Br | H | H | H | H | " | $n_D^{24}$ = 1.5955 |
| 22 | 3-Cl | H | H | H | H | " | $n_D^{23}$ = 1.5899 |
| 23 | 3-$CH_3$ | H | H | H | H | " | |
| 24 | 2-$CH_3$ | H | H | H | H | " | $n_D^{23}$ = 1.5885 |
| 25 | H | 4-$C(CH_3)_3$ | H | H | H | " | $n_D^{23}$ = 1.5730 |
| 26 | H | 4-$C(CH_3)_3$ | H | H | CN | " | |
| 27 | H | 4-$C(CH_3)_3$ | H | H | C≡CH | " | |
| 28 | H | 4-F | H | H | H | " | |
| 29 | H | 4-F | H | H | CN | " | $n_D^{21}$ = 1.5787 |
| 30 | H | 4-F | H | H | C≡CH | " | |
| 31 | 4-Cl | 4-$C(CH_3)_3$ | H | H | H | " | |
| 32 | 4-Cl | 4-$C(CH_3)_3$ | H | H | CN | " | |
| 33 | 4-Cl | 4-F | H | H | H | " | $n_D^{24}$ = 1.5750 |
| 34 | 4-Cl | 4-F | H | H | CN | " | |
| 35 | 4-$CH_3$ | 4-F | H | H | H | " | $n_D^{25}$ = 1.5686 |
| 36 | 4-$CH_3$ | 4-F | H | H | CN | " | $n_D^{20}$ = 1.5828 |
| 37 | H | H | H | Br | H | " | |
| 38 | H | H | H | Br | CN | " | $n_D^{23}$ = 1.5972 |
| 39 | H | H | H | Br | C≡CH | " | |
| 40 | H | H | H | Br | $CH_3$ | " | $n_D^{22}$ = 1.5805 |
| 41 | 4-Br | H | H | Br | H | " | |
| 42 | 4-Br | H | H | Br | CN | " | |
| 43 | 4-Br | H | H | Br | $CH_3$ | " | |
| 44 | H | H | H | $CH_3$ | H | " | $n_D^{20}$ = 1.5737 |
| 45 | H | H | H | $CH_3$ | CN | " | $n_D^{21}$ = 1.5681 |
| 46 | H | H | H | $CH_3$ | C≡CH | " | $n_D^{23}$ = 1.5808 |
| 47 | 4-Br | H | H | $CH_3$ | H | " | $n_D^{24}$ = 1.5832 |
| 48 | 4-Br | H | H | $CH_3$ | CN | " | $n_D^{22}$ = 1.5778 |
| 49 | 4-Br | H | H | $CH_3$ | C≡CH | " | |
| 50 | H | H | Br | $CH_3$ | H | " | |
| 51 | H | H | Br | $CH_3$ | CN | " | |
| 52 | 4-Br | H | Br | $CH_3$ | H | " | |
| 53 | 4-Br | H | Br | $CH_3$ | CN | " | |
| 54 | H | H | H | $C_2H_5$ | H | " | $n_D^{21}$ = 1.5720 |
| 55 | H | H | H | $C_2H_5$ | CN | " | $n_D^{20}$ = 1.5768 |
| 56 | H | H | H | $C_2H_5$ | C≡CH | " | |
| 57 | 4-Br | H | H | $C_2H_5$ | H | " | |
| 58 | 4-Br | H | H | $C_2H_5$ | CN | " | $n_D^{23}$ = 1.5818 |
| 59 | H | H | H | $C_6H_5$ | H | " | |
| 60 | H | H | H | $C_6H_5$ | CN | " | |
| 61 | H | H | H |  | H | " | |
| 62 | H | H | H |  | CN | " | |
| 63 | H | H | Cl | H | H | " | |
| 64 | H | H | Cl | H | CN | " | $n_D^{23}$ = 1.5819 |
| 65 | 4-Br | H | Cl | H | H | " | |

-continued

| Example | R¹ | R² | R³ | R⁴ | R⁵ | R⁶ | $n_D$ |
|---|---|---|---|---|---|---|---|
| 66 | 4-Br | H | Cl | H | CN | | |
| 67 | H | H | H | H | H | (2,2-dimethyl-3-(1,2-dichlorovinyl)cyclopropyl, Cl/Cl cis) | |
| 68 | H | H | H | H | CN | " | $n_D^{23} = 1.5732$ |
| 69 | H | H | H | H | C≡CH | " | $n_D^{20} = 1.5789$ |
| 70 | H | H | H | H | CH₃ | " | $n_D^{22} = 1.5715$ |
| 71 | H | H | H | CH₃ | H | " | |
| 72 | H | H | H | CH₃ | CN | " | $n_D^{25} = 1.5758$ |
| 73 | H | H | Br | CH₃ | CN | " | |
| 74 | H | H | H | Br | CN | " | |
| 75 | H | H | H | H | H | (2,2-dimethyl-3-(1,2-dibromovinyl)cyclopropyl, Br/Br cis) | $n_D^{25} = 1.5989$ |
| 76 | H | H | H | H | CN | " | $n_D^{25} = 1.5973$ |
| 77 | H | H | H | H | C≡CH | " | $n_D^{25} = 1.5953$ |
| 78 | H | H | H | H | CH₃ | " | $n_D^{20} = 1.5906$ |
| 79 | H | H | H | CH₃ | CN | " | $n_D^{20} = 1.5940$ |
| 80 | H | H | H | CH₃ | C≡CH | " | $n_D^{25} = 1.5965$ |
| 81 | H | H | H | H | H | (2,2-dimethyl-3-(2-methylprop-1-enyl)cyclopropyl, CH₃ cis/trans = 50:50) | |
| 82 | H | H | H | H | CN | " | |
| 83 | H | H | H | H | C≡CH | " | $n_D^{25} = 1.5590$ |
| 84 | H | H | H | CH₃ | CN | " | $n_D^{22} = 1.5610$ |
| 85 | 4-F | H | H | H | H | " | $n_D^{26} = 1.5578$ |
| 86 | H | H | H | H | H | (2,2-dimethyl-3-(1-bromo-2,2-dichloroethyl)cyclopropyl, Br Cl cis/trans = 50:50) | |
| 87 | H | H | H | H | CN | " | $n_D^{23} = 1.5929$ |
| 88 | H | H | H | H | C≡CH | " | |
| 89 | H | H | H | H | CH₃ | " | |
| 90 | 4-Br | H | H | H | H | " | $n_D^{22} = 1.6050$ |
| 91 | 4-Br | H | H | H | CN | " | $n_D^{22} = 1.6626$ |
| 92 | H | H | H | CH₃ | H | " | |
| 93 | H | H | H | CH₃ | CN | " | $n_D^{22} = 1.5915$ |
| 94 | 4-Br | H | H | CH₃ | H | " | |
| 95 | 4-Br | H | H | CH₃ | CN | " | |
| 96 | H | H | H | C₂H₅ | H | " | |
| 97 | H | H | H | C₂H₅ | CN | " | $n_D^{23} = 1.5840$ |
| 98 | 4-Br | H | H | C₂H₅ | H | " | |
| 99 | 4-Br | H | H | C₂H₅ | CN | " | $n_D^{22} = 1.5950$ |
| 100 | H | H | H | H | H | —CH(CH(CH₃)₂)—C₆H₄—Cl (4-Cl) | $n_D^{20} = 1.5865$ |

-continued

| Example | R¹ | R² | R³ | R⁴ | R⁵ | R⁶ | $n_D$ |
|---|---|---|---|---|---|---|---|
| 101 | H | H | H | H | CN | " | $n_D^{23} = 1.5798$ |
| 102 | H | H | H | H | C≡CN | " | $n_D^{26} = 1.5775$ |
| 103 | H | H | H | H | CH₃ | " | $n_D^{21} = 1.5738$ |
| 104 | 4-Br | H | H | H | H | " | $n_D^{22} = 1.5958$ |
| 105 | 4-Br | H | H | H | C≡CH | " | |
| 106 | 4-Br | H | H | H | CH₃ | " | |
| 107 | 4-Cl | H | H | H | H | " | $n_D^{23} = 1.5788$ |
| 108 | 4-Cl | H | H | H | CN | " | $n_D^{21} = 1.5905$ |
| 109 | 4-Cl | H | H | H | C≡CH | " | |
| 110 | 4-CH₃ | H | H | H | H | " | $n_D^{26} = 1.5809$ |
| 111 | 4-CH₃ | H | H | H | CN | " | $n_D^{20} = 1.5823$ |
| 112 | 4-CH₃ | H | H | H | C≡CH | " | |
| 113 | 4-F | H | H | H | H | " | $n_D^{26} = 1.5761$ |
| 114 | 4-F | H | H | H | CN | " | |
| 115 | 4-F | H | H | H | C≡CH | " | |
| 116 | 4-OCH₃ | H | H | H | H | " | $n_D^{20} = 1.5843$ |
| 117 | 4-OCH₃ | H | H | H | CN | " | |
| 118 | 3-Br | H | H | H | H | " | $n_D^{24} = 1.5978$ |
| 119 | 3-Cl | H | H | H | H | " | $n_D^{23} = 1.5913$ |
| 120 | 3-CH₃ | H | H | H | H | " | |
| 121 | 2-CH₃ | H | H | H | H | " | $n_D^{23} = 1.5900$ |
| 122 | H | 4-C(CH₃)₃ | H | H | H | " | $n_D^{25} = 1.5732$ |
| 123 | H | " | H | H | CN | " | |
| 124 | H | " | H | H | C≡CH | " | |
| 125 | H | 4-F | H | H | CN | " | $n_D^{21} = 1.5798$ |
| 126 | H | 4-F | H | H | CH₃ | " | |
| 127 | H | 4-F | H | H | C≡CH | " | |
| 128 | 4-Cl | 4-C(CH₃)₃ | H | H | H | " | |
| 129 | 4-Cl | 4-C(CH₃)₃ | H | H | CN | " | |
| 130 | 4-Cl | 4-F | H | H | H | " | $n_D^{24} = 1.5770$ |
| 131 | 4-Cl | 4-F | H | H | CN | " | |
| 132 | 4-CH₃ | 4-F | H | H | H | " | $n_D^{24} = 1.5714$ |
| 133 | 4-CH₃ | 4-F | H | H | CN | " | |
| 134 | H | H | H | Br | H | " | $n_D^{23} = 1.5929$ |
| 135 | H | H | H | Br | CN | " | $n_D^{23} = 1.5912$ |
| 136 | H | H | H | Br | CH₃ | " | $n_D^{22.5} = 1.5829$ |
| 137 | 4-Br | H | H | Br | H | " | |
| 138 | 4-Br | H | H | Br | CN | " | |
| 139 | 4-Br | H | H | Br | CH₃ | " | |
| 140 | H | H | H | CH₃ | H | " | $n_D^{25} = 1.5705$ |
| 141 | H | H | H | CH₃ | CN | " | $n_D^{22} = 1.5785$ |
| 142 | H | H | H | CH₃ | C≡CH | " | $n_D^{25} = 1.5814$ |
| 143 | 4-Br | H | H | CH₃ | H | " | $n_D^{24} = 1.5789$ |
| 144 | 4-Br | H | H | CH₃ | CN | " | $n_D^{24} = 1.5750$ |
| 145 | 4-Br | H | H | CH₃ | C≡CH | " | |
| 146 | H | H | Br | CH₃ | H | " | |
| 147 | H | H | Br | CH₃ | CN | " | |
| 148 | 4-Br | H | Br | CH₃ | H | " | |
| 149 | 4-Br | H | Br | CH₃ | CN | " | |
| 150 | H | H | H | C₂H₅ | H | " | $n_D^{24} = 1.5702$ |
| 151 | H | H | H | C₂H₅ | CN | " | $n_D^{20} = 1.5740$ |
| 152 | H | H | H | C₂H₅ | C≡CH | " | |
| 153 | 4-Br | H | H | C₂H₅ | H | " | |
| 154 | 4-Br | H | H | C₂H₅ | CN | " | $n_D^{23} = 1.5824$ |
| 155 | H | H | H | C₆H₅ | H | " | |
| 156 | H | H | H | C₆H₅ | CN | " | |
| 157 | H | H | H | —⟨O⟩—Cl | H | " | |
| 158 | H | H | H | —⟨O⟩—Cl | CN | " | |
| 159 | H | H | Cl | H | H | " | |
| 160 | H | H | Cl | H | CN | " | $n_D^{22} = 1.5775$ |
| 161 | 4-Br | H | Cl | H | H | " | |
| 162 | 4-Br | H | Cl | H | CN | " | |
| 163 | H | H | H | H | H | —CH—⟨O⟩—OCF₂CF₂H<br>    \|<br>   CH(CH₃)₂ | $n_D^{25} = 1.5305$ |
| 164 | H | H | H | H | CN | " | |
| 165 | H | H | H | CH₃ | CN | " | $n_D^{25} = 1.5291$ |

-continued

| Example | R¹ | R² | R³ | R⁴ | R⁵ | R⁶ | $n_D$ |
|---|---|---|---|---|---|---|---|
| 166 | H | H | H | H | H | —CH—C₆H₅<br>\|<br>CH(CH₃)₂ | $n_D^{20}$ = 1.5825 |
| 167 | H | H | H | H | CN | " | $n_D^{23}$ = 1.5758 |
| 168 | H | H | H | H | C≡CH | " | $n_D^{21}$ = 1.5689 |
| 169 | H | H | H | H | CH₃ | " | |
| 170 | 4-Br | H | H | H | H | " | $n_D^{22}$ = 1.5915 |
| 171 | 4-Br | H | H | H | CN | " | $n_D^{22}$ = 1.5884 |
| 172 | 4-Br | H | H | H | C≡CH | " | |
| 173 | 4-Br | H | H | H | CH₃ | " | |
| 174 | 4-Cl | H | H | H | H | " | $n_D^{20}$ = 1.5868 |
| 175 | 4-Cl | H | H | H | CN | " | |
| 176 | 4-Cl | H | H | H | C≡CH | " | |
| 177 | 4-CH₃ | H | H | H | H | " | $n_D^{23}$ = 1.5778 |
| 178 | 4-CH₃ | H | H | H | CN | " | |
| 179 | 4-CH₃ | H | H | H | C≡CH | " | |
| 180 | 4-F | H | H | H | H | " | $n_D^{26}$ = 1.5707 |
| 181 | 4-F | H | H | H | CN | " | |
| 182 | 4-OCH₃ | H | H | H | H | " | $n_D^{19}$ = 1.5798 |
| 183 | 4-OCH₃ | H | H | H | CN | " | |
| 184 | 3-Br | H | H | H | H | " | $n_D^{24}$ = 1.5932 |
| 185 | 3-Cl | H | H | H | H | " | $n_D^{23}$ = 1.5878 |
| 186 | 3-CH₃ | H | H | H | H | " | |
| 187 | 2-CH₃ | H | H | H | H | " | $n_D^{23}$ = 1.5819 |
| 188 | H | 4-C(CH₃)₃ | H | H | H | " | $n_D^{25}$ = 1.5682 |
| 189 | H | 4-C(CH₃)₃ | H | H | CN | " | |
| 190 | H | 4-C(CH₃)₃ | H | H | C≡CH | " | |
| 191 | H | 4-F | H | H | H | " | |
| 192 | H | 4-F | H | H | CN | " | |
| 193 | H | 4-F | H | H | C≡CH | " | |
| 194 | 4-Cl | 4-C(CH₃)₃ | H | H | H | " | |
| 195 | 4-Cl | 4-C(CH₃)₃ | H | H | CN | " | |
| 196 | 4-Cl | 4-F | H | H | H | " | |
| 197 | 4-Cl | 4-F | H | H | CN | " | |
| 198 | 4-CH₃ | 4-F | H | H | H | " | |
| 199 | 4-CH₃ | 4-F | H | H | CN | " | |
| 200 | H | H | H | Br | H | —CH—C₆H₅<br>\|<br>CH(CH₃)₃ | |
| 201 | H | H | H | Br | CN | " | |
| 202 | H | H | H | Br | CH₃ | " | $n_D^{22}$ = 1.5878 |
| 203 | 4-Br | H | H | Br | H | " | $n_D^{23}$ = 1.5785 |
| 204 | 4-Br | H | H | Br | CN | " | |
| 205 | 4-Br | H | H | Br | CH₃ | " | |
| 206 | H | H | H | CH₃ | H | " | $n_D^{25}$ = 1.5709 |
| 207 | H | H | H | CH₃ | CN | " | $n_D^{22}$ = 1.5740 |
| 208 | H | H | H | CH₃ | C≡CH | " | $n_D^{21}$ = 1.5769 |
| 209 | 4-Br | H | H | CH₃ | H | " | |
| 210 | 4-Br | H | H | CH₃ | CN | " | |
| 211 | 4-Br | H | H | CH₃ | C≡CH | —CH—C₆H₅<br>\|<br>CH(CH₃)₂ | |
| 212 | H | H | Br | CH₃ | H | " | |
| 213 | H | H | Br | CH₃ | CN | " | |
| 214 | 4-Br | H | Br | CH₃ | H | " | |
| 215 | 4-Br | H | Br | CH₃ | CN | " | |
| 216 | H | H | H | C₂H₅ | H | " | |
| 217 | H | H | H | C₂H₅ | CN | " | $n_D^{25}$ = 1.5680 |
| 218 | H | H | H | C₂H₅ | C≡CH | " | |
| 219 | 4-Br | H | H | C₂H₅ | H | " | |
| 220 | 4-Br | H | H | C₂H₅ | CN | " | $n_D^{23}$ = 1.5779 |
| 221 | H | H | H | C₆H₅ | H | " | |
| 222 | H | H | H | C₆H₅ | CN | " | |
| 223 | H | H | H | 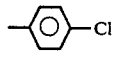 | H | " | |
| 224 | H | H | H | 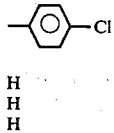 | CN | " | |
| 225 | H | H | Cl | H | H | " | |
| 226 | H | H | Cl | H | CN | " | |
| 227 | 4-Br | H | Cl | H | H | " | |

| Example | R¹ | R² | R³ | R⁴ | R⁵ | R⁶ | n_D |
| --- | --- | --- | --- | --- | --- | --- | --- |
| 228 | 4-Br | H | Cl | H | CN | " | |
| 229 | H | CF₃ | H | H | H | (As Example 3) | |
| 230 | H | H | CH₃ | H | H | " | |
| 231 | H | H | CN | H | H | " | |
| 232 | H | H | H | Cl | H | " | |

FORMULATION EXAMPLES

EXAMPLE A

A wettable powder which is easily dispersible in water is obtained by mixing, and grinding in a pin disc mill: 25 parts by weight of 3-(3-phenoxyphenyl)-2'-propen-1'-yl 3-(2,2-dichlorovinyl)-2,2-dimethylcyclopropane-1-carboxylate as the active compound, 64 parts by weight of quartz containing kaolin as an inert substance, 10 parts by weight of potassium ligninsulfonate and 1 part by weight of sodium oleylmethyltauride as wetting and dispersing agents.

EXAMPLE B

A dusting agent which is very suitable for application is obtained by mixing, and comminuting in a beater mill: 10 parts by weight of 3-(3-(4-bromophenoxy)-phenyl)-2-propen-1-yl 2-(4-chlorophenyl)-isovalerate as the active compound and 90 parts by weight of talc as an inert substance.

EXAMPLE C

An emulsifiable concentrate consists of: 15 parts by weight of 3-(3-phenoxyphenyl)-2-propen-1-yl 3-(2,2-dichlorovinyl)-2,2-dimethylcyclopropane-1-carboxylate as the active compound, 75 parts by weight of cyclohexanone as solvent and 10 parts by weight of oxethylated nonylphenol (10 EO) as the emulsifier.

EXAMPLE D

Granules consist, for example, of about 2–15 parts by weight of 3-(3-(4-bromophenoxy)-phenyl)-2-propen-1-yl 2-(4-chlorophenyl)-isovalerate as the active compound and an inert granule carrier material, such as, for example, attapulgite, pumice granules and/or quartz sand.

Biological Examples

EXAMPLE A

Diptera:

1 ml of a solution of the active compound (Example 1) in acetone, corresponding to a concentration of active compound of 0.05%, was applied uniformly to the inner faces of the lid and the base of a Petri dish by means of a pipette, and the dishes were left open until the solvent had evaporated completely. 10 house flies (Musca domestica) were then placed in each of the dishes and the latter were closed by means of the lid. Evaluation, carried out after 3 hours by counting the flies which had been killed, gave a mortality of 100%.

A similar effect was produced by the compounds of the following Examples: 3, 44, 45, 46, 48, 54, 58, 68, 76, 79, 87, 97, 99, 101, 154 and 167.

EXAMPLE B

Blattaria:

In the tests with cockroaches, the procedure followed for the pretreatment of the Petri dishes was analogous to the method used in the case of Diptera. The concentration of the active compound (Example 3) in acetone was 0.05%. After the coating of the test substances had dried on, 10 larvae (L4) of the cockroach (Blattella germanica) were placed in each Petri dish, the dishes were closed by means of the lid and the dead cockroaches were counted after 72 hours. A mortality of 100% was observed.

A similar effect was produced by the following compounds: 54, 58, 68, 76, 79, 87, 101 and 167.

EXAMPLE C

Lepidoptera:

Leaves of the cotton plant (Gossypium spec.) were sprayed with an aqueous suspension of the compound (Example 3) corresponding to an active compound concentration of 0.025% ($\doteq$ 600 l of spray liquor per hectare) and similarly treated caterpillars (10, in the L 3–4 stage) of Prodenia litura were placed on the leaves. The leaves and the caterpillars were kept together in observation cages and the mortality of the animals was determined after 2 days. It was 100%.

A similar effect was also shown by the following compounds: 1, 7, 44, 45, 46, 48, 55, 58, 68, 76, 79, 80, 86, 87, 97, 99, 101, 140, 141, 150, 167 and 207.

EXAMPLE D

Coleoptera:

Leaves of the bean plant Phaseolus vulgaris were inserted by means of the leaf-stalks into small glass bottles filled with water and their upper and lower sides were sprayed with an aqueous suspension of the compound (Example 3) corresponding to an active compound concentration of 0.025% ($\doteq$ 600 l of spray liquor per hectare). Groups of 10 larvae (24) of the Mexican bean beetle (Epilachna varivestis) were treated similarly and, after the spray coating had dried on, the treated larvae were placed on the treated leaves, in open vessels. Evaluation of the activity after 2 days gave a mortality of 100%.

The following compounds were similarly effective: 2, 7, 44, 45, 48, 54, 58, 68, 76, 79, 80, 87, 93, 97, 99, 101, 140, 141, 142, 150, 167 and 208.

EXAMPLE E

Field beans (Vicia faba) which were severely infested by bean aphids (Aphis craccivora) were sprayed to the stage of dripping off with an aqueous suspension of a wettable powder concentrate containing 0.025% by weight of the active compound from Example 2. After the plants had been placed in a greenhouse, a 100% mortality of the experimental animals was observed 3 days after treatment.

A similar activity was exhibited by the compounds according to the following Examples: 3, 7, 45, 46, 54, 58, 76, 79, 80, 87, 97, 99, 100, 101, 141, 144, 150, 154 and 167.

EXAMPLE F

Plants (small apple trees) which were severely infested by fruit tree red spider mites (*Panonychus ulmi*, resistant strain) were sprayed until the stage where dripping off began with an aqueous suspension of a wettable powder concentrate containing 0.1% by weight of the active compound (Example 3), and the plants were placed in a greenhouse.

The acaricidal activity was determined 8 days after treatment and gave a mortality of 100% for the compounds from Examples 45, 76, 79, 87 and 101.

EXAMPLE G

In vitro test on tropical cattle ticks (*Boophilus microplus*)

The following test procedure enabled the activity of the claimed compounds against ticks to be demonstrated: a suitable formulation of active compound was prepared by making a 10% strength (w/v) solution of the active compounds in a mixture consisting of dimethylformamide (85 g), nonylphenol polyglycol ether (3 g) and oxethylated castor oil (7 g), and the emulsion concentrates thus obtained were diluted with water to the test concentrations.

Ten fully bloated females of the tropical tick *Boophilus microplus* were dipped for five minutes into each of these active compound dilutions. The ticks were then dried on filter paper and were then fastened by the rear side on adhesive film so that ovi-position could take place. The ticks were kept in a warmed cabinet at 28° C. and an atmospheric humidity of 90%.

As a control, female ticks were merely dipped into water.

The activity was evaluated by determining the inhibition of ovi-position two weeks after the treatment. In this context 100% denotes that no ticks laid eggs, while 0% denotes that all the ticks laid eggs.

TABLE

| | Tick test | |
|---|---|---|
| Example | Concentration of active compound in ppm | % Inhibition of ovi-position |
| 3 | 1,000 | 100 |
| 45 | 1,000 | 100 |
| 76 | 1,000 | 100 |
| 79 | 1,000 | 100 |

We claim:

1. A compound of the formula

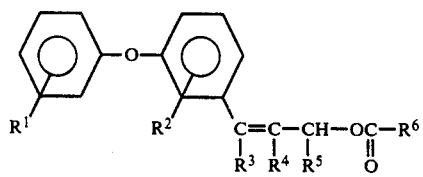

in which $R^1$ denotes hydrogen, halogen, $C_1-C_4$ alkyl or $C_1-C_4$ alkoxy, $R^2$ denotes hydrogen, halogen, $C_1-C_4$ alkyl or trifluoromethyl, $R^3$ denotes hydrogen, halogen, cyano or $C_1-C_4$ alkyl, $R^4$ denotes hydrogen, halogen, $C_1-C_4$ alkyl, phenyl or halogenophenyl, $R^5$ denotes hydrogen, $C_1-C_4$ alkyl, $C_2-C_3$ alkynyl or cyano, $R^6$ denotes a radical of the formula

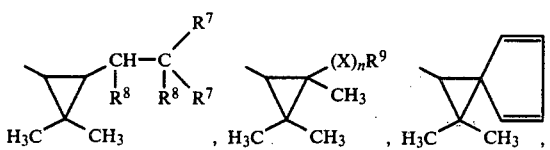

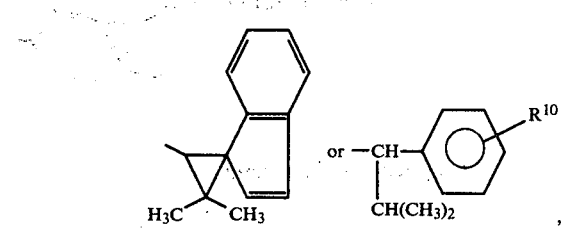

$R^7$ denotes halogen, $C_1-C_4$ alkyl, phenyl or halogenophenyl, $R^8$ denotes halogen or the two $R^8$s together denote a further chemical bond, $R^9$ denotes $C_1-C_4$ alkyl, phenyl or halogenophenyl, $R^{10}$ denotes hydrogen, halogen, $C_1-C_4$ alkyl, $C_1-C_4$ alkoxy, $C_1-C_4$ alkylthio, halogeno-($C_1-C_4$) alkoxy, halogeno-($C_1-C_4$) alkylthio or methylenedioxy, X denotes oxygen or sulfur and n denotes 0 or 1.

2. A compound of the formula I in the form of its optical enantiomers and/or its stereoisomers.

3. A compound of the formula

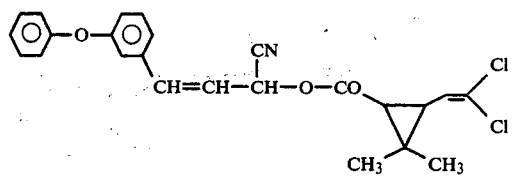

4. A compound of the formula

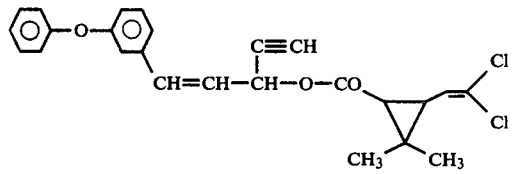

5. A compound of the formula

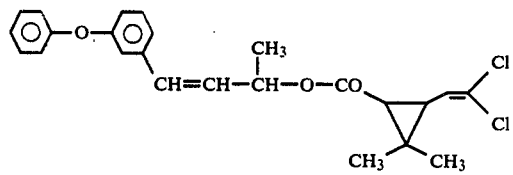

6. A compound of the formula

7. A compound of the formula

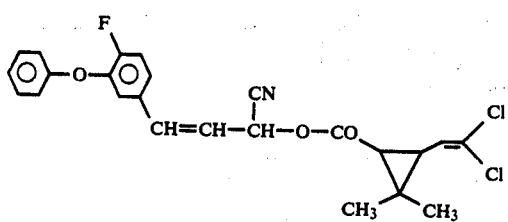

8. A compound of the formula

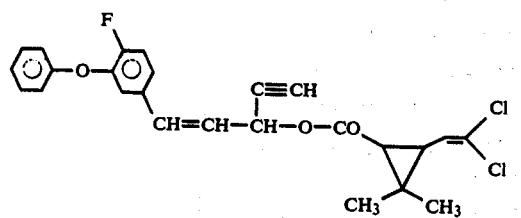

9. A compound of the formula

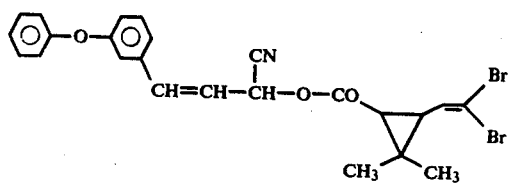

10. A compound of the formula

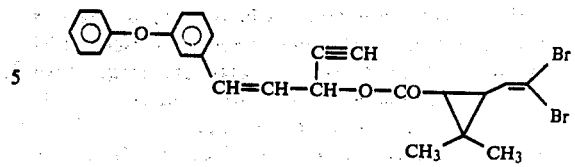

11. A compound of the formula

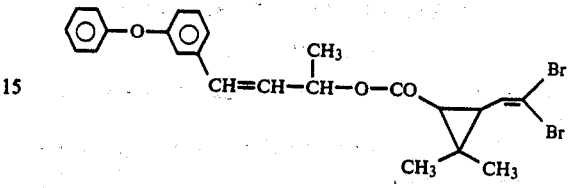

12. A compound of the formula

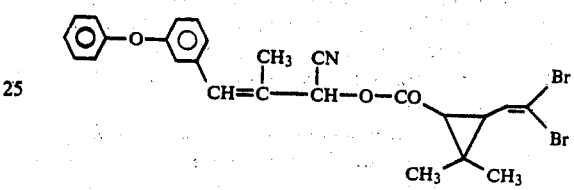

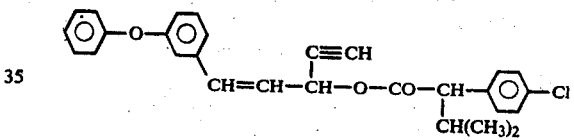

13. An insecticidal and acaricidal composition containing an effective amount of a compound defined in claim 1 or 2, and a carrier material therefor.

14. A process for combating harmful insects or acarids, which comprises applying to them or to a substrate attacked by them an insecticidally or acaricidally effective amount of a compound defined in claim 1 or 2.

* * * * *